United States Patent
Gotsche et al.

(10) Patent No.: US 6,579,953 B1
(45) Date of Patent: *Jun. 17, 2003

(54) APPLICATION OF WATER-SOLUBLE OR WATER-DISPERSIBLE POLYMERIZATES WHICH CONTAIN POLY-ETHER AND WHICH ARE USED AS A COATING AGENT, A BINDING AGENT AND/OR AS A FILM-FORMING AUXILIARY AGENT IN PHARMACEUTICAL FORMS OF ADMINISTRATION

(75) Inventors: Michael Gotsche, Aachen (DE); Karl Kolter, Limburgerhof (DE); Axel Sanner, Frankenthal (DE); Maximilian Angel, Schifferstadt (DE); Alfred Leinenbach, Gönnheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/787,956

(22) PCT Filed: Sep. 24, 1999

(86) PCT No.: PCT/EP99/07123

§ 371 (c)(1),
(2), (4) Date: Mar. 23, 2001

(87) PCT Pub. No.: WO00/18375

PCT Pub. Date: Apr. 6, 2000

(30) Foreign Application Priority Data

| | | |
|---|---|---|
| Sep. 30, 1998 | (DE) | 198 44 903 |
| Feb. 11, 1999 | (DE) | 199 05 906 |
| Jul. 8, 1999 | (DE) | 199 31 667 |

(51) Int. Cl.$^7$ .................. C08F 283/06; C08F 218/08
(52) U.S. Cl. .................. 525/451; 525/71; 525/531; 525/438; 525/496; 525/407; 525/408; 525/409; 525/418
(58) Field of Search .................. 525/451, 71, 531, 525/438, 439, 496, 407, 408, 409, 418

(56) References Cited

U.S. PATENT DOCUMENTS

| | | |
|---|---|---|
| 3,984,494 A | 10/1976 | Harreus |
| 4,224,427 A | 9/1980 | Mueller |
| 4,548,990 A | 10/1985 | Mueller |
| 4,873,086 A | 10/1989 | Good |
| 5,478,884 A | 12/1995 | Tomita |
| 6,239,228 B1 * | 5/2001 | Zajaczkowski et al. ...... 525/302 |

FOREIGN PATENT DOCUMENTS

| | | |
|---|---|---|
| DE | 1 077 430 | 9/1960 |
| DE | 1 081 229 | 11/1960 |
| DE | 11094457 | 6/1961 |
| DE | 23 63 853 | 7/1975 |
| DE | 4336493 | 4/1994 |
| EP | 524 786 | 1/1993 |
| EP | 743 962 | 11/1996 |
| EP | 797 987 | 10/1997 |
| GB | 922 457 | 4/1963 |
| GB | 922458 | 4/1963 |
| GB | 922 459 | 4/1963 |

OTHER PUBLICATIONS

J.Soc.CosmeticChem. Bd.5,1954 249ff.
Pharmazie in unserer Zeit, 1994, 23(4),226–229,Knop.

* cited by examiner

Primary Examiner—James J. Seidleck
Assistant Examiner—Olga Asinovsky
(74) Attorney, Agent, or Firm—Keil & Weinkauf

(57) ABSTRACT

The use of polymers which are obtainable by polymerization of
a) at least one vinyl ester of aliphatic $C_1$–$C_{24}$-carboxylic acids in the presence of
b) polyethers of the general formula I,

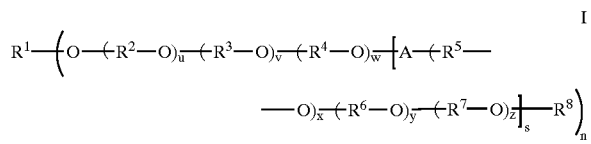

in which the variables have, independently of one another, the meanings mentioned in the description, as coating agent, binder and/or film-forming excipient in pharmaceutical presentations.

19 Claims, No Drawings

APPLICATION OF WATER-SOLUBLE OR WATER-DISPERSIBLE POLYMERIZATES WHICH CONTAIN POLY-ETHER AND WHICH ARE USED AS A COATING AGENT, A BINDING AGENT AND/OR AS A FILM-FORMING AUXILIARY AGENT IN PHARMACEUTICAL FORMS OF ADMINISTRATION

The invention relates to the use of water-soluble or water-dispersible polyether-containing polymers as coating agent, binder and/or film-forming excipient in pharmaceutical presentations.

Solid pharmaceutical presentations such as tablets, capsules, pellets, granules, crystals etc. are provided with a film coating for a wide variety of reasons. It is possible in this way, for example, to mask an unpleasant odor or taste, and improve the swallowability. The stability of the active ingredient can be increased by the coating, since less water vapor and oxygen reaches the interior of the tablets. The presentations have a better appearance and can be distinguished better by incorporating dyes. In addition, in particular the rate of release of the active ingredient can be adjusted by the film coating.

A distinction is made in general between instant release forms and slow release forms.

In the case of instant release forms, the disintegration of the tablet and the release of the active ingredient from the presentation should, where possible, be unaffected by the coating, for which reason the film coating must dissolve rapidly in gastric fluid. In addition, it must have good film properties. The tensile strength and the ultimate elongation should be high so that the film coating withstands mechanical effects like those occurring during pharmaceutical processing—especially packaging—and during transport and storage.

A product which is frequently employed for coating instant release tablets is hydroxypropylmethylcellulose (HPMC). Hydroxypropylmethylcellulose shows a steep rise in viscosity with increasing concentration in aqueous solution. Hydroxypropylcellulose (HPC) also shows a similar behavior.

Since the film former solution must be finely atomized for coating tablets, and the drops which are formed must thoroughly wet the surface of the tablets, and moreover spread well, the viscosity must not exceed a certain limit (between 150 and 250 mPas) which depends on the type of spray nozzle and the equipment. It is therefore possible in the case of HPMC to employ only relatively low film former concentrations.

The recommendation given in the literature for the concentration of Pharmacoat® 606 (from Shin-etsu) is 5 to 7% by weight (Pharmaceutical Coating Technology, edited by Graham Cole, Taylor and Francis Ltd. 1995 and manufacturers' technical data sheet). These low spray concentrations result in relatively long processing times and thus high costs.

In addition, hydroxypropylmethylcellulose has other disadvantages, inter alia in the wetting characteristics, in the adhesiveness on the tablet surface, in the pigment binding capacity, in the mechanical properties of the films, in the hygroscopicity and in the permeability for water vapor and oxygen, in the rate of dissolution and in the difference in disintegration time between film-coated tablets and core.

The low elasticity of hydroxypropylmethylcellulose films frequently leads to the film-coated tablets splitting open on storage in moist conditions, as a consequence of the swelling of the core. Even the use of plasticizers results in negligible improvements in this problem. On the contrary, it might lead to tacky films and, through migration, to changes in the tablet properties.

Oral drug forms which release the medicinal substance over a lengthy period with the aim of prolonging the effect of the active component (generally slow release drug forms) are becoming increasingly important. They are associated with the advantages of improved patient compliance through a reduced frequency of intake, a reduction in side effects through avoidance of plasma peaks, more uniform blood levels of the medicinal substance, and the avoidance of local irritation. Besides the formulation of medicinal substance-containing cores which are coated with a film which is insoluble in water but is semipermeable or contains pores through which the medicinal substance diffuses, release can be controlled and prolonged by embedding the medicinal substance in matrices. It is possible in addition to use ion exchange resins and therapeutic systems (e.g. OROS).

Embedding of the medicinal substance in hydrocolloid matrices in particular provides the advantages of simple and low-cost manufacture and a high degree of drug safety because no dose dumping effects can occur. The excipients normally employed for this purpose such as hydroxypropylmethylcellulose (HPMC), hydroxypropylcellulose, alginic acid or alginates, and xanthan have disadvantages on use. Those which may be mentioned are: deficient flow properties which makes direct tableting difficult, a dependence of the release of medicinal substance on the osmolarity (salt content) and on the pH of the release medium. This applies equally to HPMC and to hydroxypropylcellulose, xanthan and alginates. The use of xanthan moreover results in tablets whose hardness is low, and the direct tableting of alginates results in compacts with only slight release-slowing properties (max. 8 h). The natural swelling substances (e.g. alginates) show overall a wide variability between batches.

It has been found, surprisingly, that the polymers described hereinafter do not have these disadvantages and are advantageous for use as matrix for release of the active ingredient in oral pharmaceutical preparations.

Binders are employed in pharmaceutical presentations in order to increase the processability and the mechanical strength. They are normally employed in tablets, granules and pellets and result in improved flowability, greater hardness and less friability.

The binders used at present such as maltodextrin or polyvinylpyrrolidones frequently do not result in satisfactory hardnesses and friabilities. Other binders such as starch paste and hydroxypropylmethylcellulose (HPMC) can be employed only in low concentrations because of their high viscosity.

In addition, film-forming excipients are employed in solutions and sprays which are applied to the skin or mucous membrane or else introduced systemically into the body. Examples thereof are preparations for wound treatment and spray-on dressings, but also preparations for application to intact skin or mucous membrane. In this case, the skin is protected by a film, and the active ingredients can penetrate into or through the skin.

Great flexibility is necessary for transdermal therapeutic systems and for wound plasters, just as for the abovementioned presentations, but the products available at present do not have this. The use of possible plasticizers to achieve the necessary flexibility is undesirable for toxicological and pharmacological reasons.

It is an object of the present invention to provide water-soluble or water-dispersible polymers as coating agents, binders and/or film-forming excipients in pharmaceutical presentations which do not have the abovementioned disadvantages.

We have found that this object is achieved by the use of polymers, in particular polymers which are soluble or dispersible in water and are obtainable by polymerization of a) at least one vinyl ester of aliphatic $C_1$–$C_{24}$-carboxylic acids, in the presence of b) polyethers of the general formula I,

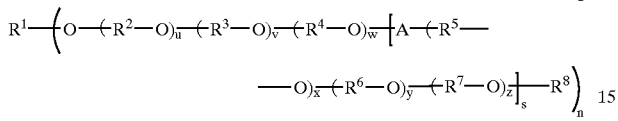

in which the variables have, independently of one another, the following meanings:

$R^1$ hydrogen, $C_1$–$C_{24}$-alkyl, $R^9$—C(=O)—, $R^9$—NH—C(=O)—, polyalcohol residue;

$R^8$ hydrogen, $C_1$–$C_{24}$-alkyl, $R^9$—C(=O)—, $R^9$—NH—C(=O)—;

$R^2$ to $R^7$
—(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—, —CH$_2$—CHOR$^{10}$—CH$_2$—;

$R^9$ $C_1$–$C_{24}$-alkyl;

$R^{10}$ hydrogen, $C_1$–$C_{24}$-alkyl, $R^9$—C(=O)—;

A —C(=O)—O—, —C(=O)—B—C(=O)—O—, —C(=O)—NH—B—NH—C(=O)—O—;

B —(CH$_2$)$_t$—, arylene, optionally substituted;

n 1 to 8;
s 0 to 500;
t 1 to 12;
u 1 to 5000;
v 0 to 5000;
w 0 to 5000;
x 1 to 5000;
y 0 to 5000;
z 0 to 5000 as coating agent, binder and/or film-forming excipient in pharmaceutical presentations.

Graft polymers containing polyalkylene oxides have already been disclosed inter alia as ancillary substances in pharmaceutical preparations.

Thus, DE-A-23 63 853 describes the use of partially hydrolyzed graft copolymers of vinyl acetate onto polyethylene glycol for producing self-supporting packs or capsules for medicines. These capsules produced from the graft copolymers are intended to be employed as alternatives to known hard gelatin capsules as described, for example, in Pharmazie in unserer Zeit, 23(4), 226–229 (1994). There is no mention in this publication of the use of graft copolymers as coating agents or binders for pharmaceutical presentations.

DE 1 077 430, DE 1 094 457 and DE 1 081 229 describe processes for producing graft copolymers of polyvinyl esters and their use as water-soluble packaging films and as ancillary substances in cosmetics.

DE 43 36 493 describes water-soluble oxyalkylene group-containing polyvinyl alcohol resin compositions and their use for example as packing materials.

The polymers used according to the invention are graft copolymers in which in general polyethers of the general formula I selected from the group consisting of polyalkylene oxides based on ethylene oxide, propylene oxide and butylene oxide, and polyglycerol, are used as grafting base b). Depending on the nature of the monomer building blocks, the resulting polymers have the following structural units.

—(CH$_2$)$_2$—O—, —(CH$_2$)$_3$—O—, —(CH$_2$)$_4$—O—, —CH$_2$—CH(CH$_3$)—O—, —CH$_2$—CH(CH$_2$—CH$_3$)—O—, —CH$_2$—CHOR$^7$—CH$_2$—O—;

These may be both homopolymers and copolymers, and the copolymers may have a random distribution or be in the form of block copolymers.

Depending on the degree of grafting, the polymers used according to the invention comprise both pure graft copolymers and mixtures of the abovementioned graft copolymers with ungrafted polyethers of the formula I and homo- or copolymers of monomers a) and, where appropriate, other monomers c).

The terminal primary hydroxyl groups in the polyethers produced on the basis of alkylene oxides or glycerol and, in addition, the secondary OH groups of polyglycerol can be both in free, unprotected form and etherified with alcohols with a chain length of $C_1$–$C_{24}$ or esterified with carboxylic acids with a chain length of $C_1$–$C_{24}$.

Alkyl radicals which may be mentioned for $R^1$ and $R^8$ to $R^{10}$ are branched or unbranched $C_1$–$C_{24}$-alkyl chains, preferably methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Preferred representatives which may be mentioned of the abovementioned alkyl radicals are branched or unbranched $C_1$–$C_{12}$-, particularly preferably $C_1$–$C_6$-alkyl chains.

The number average molecular weight of the polyethers is in the range below 500000, preferably in the range from 300 to 100000, particularly preferably in the range from 500 to 20000, very particularly preferably in the range from 800 to 15000.

It is advantageous to use homopolymers of ethylene oxide or copolymers with an ethylene oxide content of from 40 to 99% by weight. Thus, the content of ethylene oxide units in the ethylene oxide polymers to be preferably employed is from 40 to 100 mol %. Suitable as comonomers for these copolymers are propylene oxide, butylene oxide and/or isobutylene oxide. Suitable examples are copolymers of ethylene oxide and propylene oxide, copolymers of ethylene oxide and butylene oxide, and copolymers of ethylene oxide, propylene oxide and at least one butylene oxide. The ethylene oxide content in the copolymers is preferably from 40 to 99 mol %, the propylene oxide content is from 1 to 60 mol % and the butylene oxide content in the copolymers is from 1 to 30 mol %. Not only straight-chain but also branched homo- or copolymers can be used as grafting base.

Branched polymers can be produced by, for example, addition of ethylene oxide and, where appropriate, also propylene oxide and/or butylene oxides or polyglycerol onto low molecular weight polyalcohol residues (=$R^1$ in the general formula I, such as, for example, pentaerythritol, glycerol or sugars or sugar alcohols such as sucrose, D-sorbitol and D-mannitol).

The polymers which may be formed in these cases are ones in which at least one, preferably one to eight, particularly preferably one to five, of the hydroxyl groups present in the polyalcohols can be linked in the form of an ether linkage to the following polyether residue P as shown in formula I

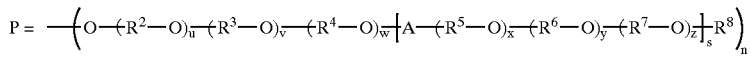

$n = 1$ to $8$

The alkylene oxide units may be randomly distributed or present in the form of blocks in the polymer.

However, it is also possible to use polyesters of polyalkylene oxides and aliphatic $C_1$–$C_{12}$-, preferably $C_1$–$C_6$-dicarboxylic acids or aromatic dicarboxylic acids, e.g. oxalic acid, succinic acid, adipic acid or terephthalic acid with molecular weights of from 1500 to 25000, described in EP-A-0 743 962, as grafting base.

It is also possible to use polycarbonates produced by phosgenation of polyalkylene oxides or polyurethanes from polyalkylene oxides and aliphatic $C_1$–$C_{12}$-, preferably $C_1$–$C_6$-diisocyanates or aromatic diisocyanates, e.g. hexamethylene diisocyanate or phenylene diisocyanate, as grafting base. The abovementioned polyesters, polycarbonates or polyurethanes may contain up to 500, preferably up to 100, polyalkylene oxide units, it being possible for the polyalkylene oxide units to consist both of homopolymers and of copolymers of different alkylene oxides.

The polymers preferably used are obtainable by polymerization of a) at least one vinyl ester of aliphatic $C_1$–$C_{24}$-carboxylic acids in the presence of b) polyethers of the general formula I,
  in which the variables have, independently of one another, the following meanings:
  $R^1$ hydrogen, $C_1$–$C_{24}$-alkyl, $R^9$—C(=O)—, polyalcohol residue;
  $R^8$ hydrogen, $C_1$–$C_{24}$-alkyl, $R^9$—C(=O)—;
  $R^2$ to $R^4$
   —(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—, —CH$_2$—CHOR$^{10}$—CH$_2$—;
  $R^9$ $C_1$–$C_{24}$-alkyl;
  $R^{10}$ hydrogen, $C_1$–$C_{24}$-alkyl, $R^9$—C(=O)—;
  n 1 to 8;
  s 0;
  u 1 to 5000;
  v 0 to 5000;
  w 0 to 5000.

The polymers particularly preferably used are obtainable by polymerization of a) at least one vinyl ester of aliphatic $C_1$–$C_{12}$-carboxylic acids, in the presence of b) polyethers of the general formula I with a number average molecular weight of from 300 to 100,000, in which the variables have, independently of one another, the following meanings:
  $R^1$ hydrogen, $C_1$–$C_{12}$-alkyl, polyalcohol residue;
  $R^8$ hydrogen, $C_1$–$C_{12}$-alkyl;
  $R^2$ to $R^4$
   —(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—, —CH$_2$—CHOR$^{10}$—CH$_2$—;
  $R^{10}$ hydrogen, $C_1$–$C_{12}$-alkyl;
  n 1 to 5;
  s 0;
  u 2 to 2000;
  v 0 to 2000;
  w 0 to 2000.

The polymers very particularly preferably used are obtainable by polymerization of a) at least one vinyl ester of aliphatic $C_1$–$C_6$-carboxylic acids, in particular vinyl acetate, in the presence of b) polyethers of the general formula I with a number average molecular weight of from 500 to 20,000, in which the variables have, independently of one another, the following meanings:
  $R^1$, $R^8$
   hydrogen, $C_1$–$C_6$-alkyl, in particular hydrogen;
  $R^2$ to $R^4$
   —(CH$_2$)$_2$—, —(CH$_2$)$_3$—, —CH$_2$—CH(CH$_3$)—, —CH$_2$—CHOR$^{10}$—CH$_2$—, in particular —(CH$_2$)$_2$—;
  $R^{10}$ hydrogen, $C_1$–$C_6$-alkyl;
  n 1;
  s 0;
  u 5 to 500;
  v 0 to 500, in particular 0;
  w 0 to 500, in particular 0.

Component a) which may be mentioned for polymerization in the presence of polyethers of the formula I comprises the following copolymerizable monomers:

vinyl esters of aliphatic, saturated or unsaturated $C_1$–$C_{24}$-carboxylic acids, such as, for example, formic acid, acetic acid, propionic acid, butyric acid, valeric acid, isovaleric acid, caproic acid, caprylic acid, capric acid, undecylenic acid, lauric acid, myristic acid, palmitic acid, palmitoleic acid, stearic acid, oleic acid, arachic acid, behenic acid, lignoceric acid, cerotic acid and melissic acid.

Vinyl esters of the abovementioned $C_1$–$C_{12}$-carboxylic acids, in particular the $C_1$–$C_6$-carboxylic acids, are preferably used.

It is, of course, also possible for mixtures of the respective monomers in group a) to be graft copolymerized.

The hydrophobic monomers may moreover be employed mixed with one or more likewise hydrophobic comonomers, for example esters which are difficult to hydrolyze of unsaturated carboxylic acids and/or alkyl ethers, it being necessary to restrict the maximum content of these additional monomers to 30%. Contents of from 1 to 20% are preferred.

Additional monomers which can be employed for the polymerization inter alia comprise at least one other component c) selected from the group of c$_1$) $C_1$–$C_{24}$-alkyl esters of monoethylenically unsaturated $C_3$–$C_8$-carboxylic acids;

c$_2$) $C_1$–$C_{24}$-hydroxyalkyl esters of monoethylenically unsaturated $C_3$–$C_8$-carboxylic acids;

c$_3$) $C_1$–$C_{24}$-alkyl vinyl ethers;

c$_4$) N-vinyllactams;

c$_5$) monoethylenically unsaturated $C_3$–$C_8$-carboxylic acids.

A suitable monoethylenically unsaturated $C_3$–$C_8$-carboxylic acid is acrylic acid, methacrylic acid, maleic acid, fumaric acid, itaconic acid or aconitic acid.

Alkyl radicals which may be mentioned are branched or unbranched $C_1$–$C_{24}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl and the hydroxylated derivatives thereof.

Branched or unbranched $C_1$–$C_4$-alkyl chains are preferred, in particular methyl, ethyl, n-propyl, 1-methylethyl, n-butyl, 1-methylpropyl, 2-methylpropyl, 1,1-dimethylethyl and the hydroxylated derivatives thereof.

Particularly preferred monomers $c_1$–$c_3$) are methyl (meth)acrylate, ethyl (meth)acrylate, hydroxymethyl (meth)acrylate, 2-hydroxyethyl (meth)acrylate, methyl vinyl ether and ethyl vinyl ether.

The hydrophobic monomers may moreover be employed mixed with one or more hydrophilic comonomers. Those which can be used are monoethylenically unsaturated $C_3$–$C_8$-carboxylic acids such as acrylic acid, methacrylic acid, maleic acid, fumaric acid, itaconic acid, aconitic acid, as well as N-vinyllactams such as N-vinylpyrrolidone, N-vinylimidazole or N-vinylcaprolactam.

Preferred hydrophilic comonomers are (meth)acrylic acid and N-vinylpyrrolidone.

The K values of the polymers should be in the range from 10 to 200, preferably 15 to 150, particularly preferably 15 to 100, very particularly preferably in the range from 20 to 80. The K value desired in each case can be adjusted in a manner known per se by the composition of the starting materials. The K values are determined by the method of Fikentscher, Cellulosechemie, Vol. 13, pp. 58 to 64 and 71 to 74 (1932) in N-methylpyrrolidone at 25° C. and polymer concentrations between 0.1% by weight and 5% by weight, depending on the K value range.

The polymers can be prepared by polymerizing the monomers of component a) in the presence of the polyethers by using initiators which form free radicals and by the action of high-energy radiation, which is to be understood to include the action of high-energy electrons.

The polymerization can be, for example, a solution polymerization, bulk polymerization, emulsion polymerization, inverse emulsion polymerization, suspension polymerization, inverse suspension polymerization or precipitation polymerization, without the methods which can be used being restricted thereto.

The procedure for the bulk polymerization, which is preferred, can be such that the polyalkylene oxide is dissolved in at least one monomer of group a) and, after addition of a polymerization initiator, the mixture is completely polymerized. The graft copolymerization can also be carried out semicontinuously by firstly mixing part, e.g. 10%, of the mixture to be polymerized consisting of polyalkylene oxide, at least one monomer of group a) and initiator, heating the mixture to the polymerization temperature and, after the polymerization has started, adding the remainder of the mixture to be polymerized as the polymerization proceeds. The graft copolymers can also be obtained by introducing the polyalkylene oxides of group b) into a reactor and heating to the polymerization temperature, and adding at least one monomer of group a) and polymerization initiator, either all at once, batchwise or, preferably, continuously, and polymerizing.

The ratio of the amounts of the polyethers used as grafting base and the vinyl esters employed is in the range from 1:0.5 to 1:50, preferably in the range from 1:1.5 to 1:35, particularly preferably in the range from 1:2 to 1:30.

Particularly suitable polymerization initiators are organic peroxides such as diacetyl peroxide, dibenzoyl peroxide, succinyl peroxide, di-tert-butyl peroxide, tert-butyl perbenzoate, tert-butyl perpivalate, tert-butyl permaleate, cumene hydroperoxide, diisopropyl peroxydicarbonate, bis (o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, and mixtures of said initiators, redox initiators and azo initiators.

The amounts used of the initiator or initiator mixtures are, based on monomer employed, between 0.01 and 10% by weight, preferably between 0.3 and 5% by weight.

The graft copolymerization takes place at a temperature in the range from 40 to 200° C., preferably in the range from 50 to 140° C., particularly preferably in the range from 60 to 110° C. It is normally carried out under atmospheric pressure, but may also take place under reduced or elevated pressure, preferably between 1 and 5 bar.

If required, the graft copolymerization described above can also be carried out in a solvent. Examples of suitable solvents are alcohols such as methanol, ethanol, n-propanol, isopropanol, n-butanol, sec-butanol, tert-butanol, n-hexanol and cyclohexanol, and glycols such as ethylene glycol, propylene glycol and butylene glycol, and the methyl or ethyl ethers of the dihydric alcohols, diethylene glycol, triethylene glycol, glycerol and dioxane. The graft copolymerization can also be carried out in water as solvent. In this case, a solution which, depending on the amount of added monomers of component a), is more or less readily soluble in water is initially present. In order to convert water-insoluble products, which may arise during the polymerization, into a solution, it is possible, for example, to add organic solvents such as monohydric alcohols having 1 to 3 carbon atoms, acetone or dimethylformamide. However, the procedure for graft copolymerization in water can also be such that the water-insoluble graft copolymers are converted into a fine-particle dispersion by adding conventional emulsifiers or protective colloids, e.g. polyvinyl alcohol.

The emulsifiers used are, for example, ionic or nonionic surfactants whose HLB is in the range from 3 to 13. For the definition of HLB, reference is made to the publication by W. C. Griffin, J. Soc. Cosmetic Chem., Volume 5, 249 (1954).

The amount of surfactants, based on the graft copolymer, is from 0.1 to 5% by weight. Solutions or dispersions of the graft copolymers are obtained on use of water as solvent. Where solutions of the graft copolymer in an organic solvent or in mixtures of an organic solvent and water are prepared, from 5 to 200, preferably 10 to 100, parts by weight of organic solvent or of the solvent mixture are used per 100 parts by weight of the graft copolymer.

To increase the hydrophilicity of the polymers used according to the invention, ester groups can be (partially) hydrolyzed after the polymerization. The hydrolysis takes place in a manner known per se by adding a base, preferably by adding a methanolic solution of sodium or potassium hydroxide at temperatures in the range from 10 to 50° C., preferably in the range from 15 to 30° C. The degree of hydrolysis depends on the amount of base employed, on the hydrolysis temperature and on the hydrolysis time.

The degree of hydrolysis of the polyvinyl ester groups can thus be in the range from 0 to 100%. It is preferably in the range from 20 to 100%, particularly preferably in the range from 40 to 100%, especially from 65 to 100% and very particularly preferably in the range from 80 to 100%.

The solids content of the resulting aqueous polymer dispersions or solutions is usually from 10 to 70% by weight, preferably 15 to 65% by weight, particularly preferably 20 to 60% by weight.

Depending on the degree of hydrolysis and the concentration, aqueous dispersions or solutions of the polymers used according to the invention are obtained with a viscosity of less than 1000 mPas, preferably with a viscosity of from 5 to 400 mPas, particularly preferably from 10 to 250 mPas, at a polymer concentration of 20% by weight.

The polymer dispersions or solutions can be converted into powder form by various drying processes such as spray drying, fluidized spray drying, drum drying or freeze-drying. Spray drying is preferably employed as drying process owing to the advantageous low viscosity of the polymer solutions or dispersions. An aqueous dispersion or solution can be prepared anew from the resulting dry polymer powder by redispersion in water. Conversion into powder form has the advantage that storability is improved, transportability is simpler and the tendency to be attacked by microbes is reduced.

The water-soluble or water-dispersible polyalkylene oxide or polyglycerol-containing polymers are outstandingly suitable as film former, binder, wetting aid and/or solubilizer, which is soluble or dispersible in gastric fluid, for pharmaceutical presentations.

The exceptional flexibility and the low viscosity means that no additional plasticizer is usually necessary.

The invention therefore also relates to pharmaceutical presentations comprising at least one water-soluble or water-dispersible polymer as coating agent, binder and/or film-forming excipient, the polymer being obtainable by polymerization of a) at least one vinyl ester of aliphatic $C_1$–$C_{24}$-carboxylic acids in the presence of b) polyethers of the general formula I,

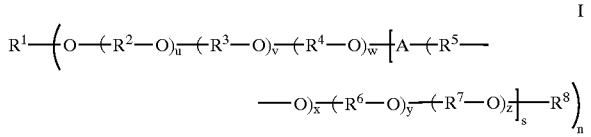

in which the variables have, independently of one another, the following meanings:

$R^1$ hydrogen, $C_1$–$C_{24}$-alkyl, $R^9$—C(=O)—, $R^9$—NH—C(=O)—, polyalcohol residue;
$R^8$ hydrogen, $C_1$–$C_{24}$-alkyl, $R^9$—C(=O)—, $R^9$—NH—C(=O)—;
$R^2$ to $R^7$
—(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—, —CH$_2$—CHOR$^{10}$—CH$_2$—;
$R^9$ $C_1$–$C_{24}$-alkyl;
$R^{10}$ hydrogen, $C_1$–$C_{24}$-alkyl, $R^9$—C(=O)—;
A —C(=O)—O—, —C(=O)—B—C(=O)—O—, —C(=O)—NH—B—NH—C(=O)—O—;
B —(CH$_2$)$_t$—, arylene, optionally substituted;
n 1 to 8;
s 0 to 500;
t 1 to 12;
u 1 to 5000;
v 0 to 5000;
w 0 to 5000;
x 1 to 5000;
y 0 to 5000;
z 0 to 5000.

For a more detailed illustration of the graft copolymers, including the variables and the preferred embodiments thereof, reference may be made to the description given at the outset.

The coated presentations are preferably inter alia film-coated tablets, film-coated microtablets, sugar-coated tablets, coated pastilles, capsules, crystals, granules or pellets.

The binder-containing presentations are preferably inter alia tablets, microtablets, cores, granules or pellets.

The polymers according to the invention can also be used to produce solutions and sprays which, applied to the skin or mucous membrane, form a film. Owing to the exceptional elasticity and adhesiveness, the films adhere for a long time to the skin or mucous membrane. The frequency of application can thus be reduced, and the comfort of wearing is increased. Examples thereof are spray-on dressings for wounds, disinfectant sprays, solutions with mycostatics, sprays or solutions for the mouth with antibiotics etc. The flexibility also means that use for transdermal therapeutic systems is advantageous.

The graft copolymers used according to the invention easily wet lipophilic surfaces and have excellent protective colloid properties. Incorporated into suspensions and emulsions, they attach themselves to the particles of the disperse phase and stabilize it. They can therefore be used as wetting aids and stabilizers in disperse systems.

They improve the solubility and rate of dissolution of medicinal substances of low solubility in water by interacting with them, whereby the absorbability and bioavailability of the medicinal substances are improved. This advantageous effect is evident, for example, with presentations in which the active ingredient is not present in solution, such as, for example, tablets, granules, suspensions etc.

The polymers used according to the invention can, where appropriate also in combination with other excipients, be processed together with active ingredients to polymer/active ingredient melts which either undergo extrusion and calendering to give drug products or, after the extrusion, are converted into granules or powders and only then processed to drug forms, for example compressed to tablets. In these cases, the graft copolymers introduce the properties detailed above into the presentation.

The polymers according to the invention are able to fulfil the following functions in an outstanding manner in various pharmaceutical presentations:

dispersing aid, suspending aid, wetting agent, solubilizer for medicinal substances of low solubility, emulsifier, crystallization inhibitor, anticaking aid, protective colloid, bioadhesive to prolong and intensify contact with the mucous membrane, spreading aid, viscosity regulator, excipient for producing solid solutions with medicinal substances, excipient for adjusting the release of active ingredient in slow release formulations.

The polymers according to the invention which are of only low solubility or insoluble but dispersible in water can also be used as release-slowing polymers and as adhesives for active ingredient plasters.

When used to produce suppositories and pessaries, the polymers on the one hand ensure the flexibility of the presentation, and on the other hand promote the disintegration and dissolution of active ingredient, and they coat the mucous membrane with an active ingredient-containing film which enhances absorption.

As shown in Table 1, the aqueous solutions of the (partly) hydrolyzed polymers according to the invention have a distinctly lower viscosity than corresponding solutions of hydroxypropylmethylcellulose.

TABLE 1

| Polymer | Viscosity (20% by weight aqueous solution) [mPas] | Flexibility Ultimate elongation [%] |
|---|---|---|
| PEG 6000/VAc (Example 1) | 124 | 74 |
| PEG 6000/VAc (Example 2) | 181 | 172 |
| PEG 9000/VAc (Example 3) | 199 | 225 |
| Polyglycerol 2200/VAc (Example 4) | 199 | 313 |
| Lutrol ® F 68/VAc (Example 5) | 145 | 110 |
| PEG 6000/VAc/MMA (Example 6) | 144 | 122 |
| Pharmacoat ® 606 (Comparison) | 5168 | 15 |

It is thus possible to employ more concentrated polymer preparations when coating tablets with the polymer dispersions, as well as for binder applications, which allows the processes to be made considerably more cost effective and time-saving.

The dissolution or redispersion of the polymers in powder or granule form to aqueous dispersions or solutions takes place considerably more quickly than with other film formers or binders, because the polymers according to the invention are thoroughly wetted by water and show little agglomeration and a very high dissolution rate.

Gastric fluid-soluble tablets coated with the (partly) hydrolyzed polymers according to the invention show a disintegration time which is only slightly longer than for the core, i.e. the film coating dissolves very rapidly in simulated gastric fluid.

In the case of the Pharmacoat 606 type of hydroxypropylmethylcellulose as coating material, disintegration takes distinctly longer (see Examples 7 and 8 with their respective comparative examples). In addition, the mechanical strength of the tablets is increased very much more when the polymers are used according to the invention than when hydroxypropylmethylcellulose is used.

Tablets swell to different extents depending on the excipients and active ingredients used, the storage time and the storage conditions, such as temperature and humidity. A rigid film coating develops cracks when the core swells. The elasticity of film formers is therefore an important quantity. Graft copolymers have exceptionally high flexibility and elasticity. Thus, the ultimate elongation may be up to 300%. No crack formation is therefore to be expected, even if the core swells greatly.

The graft copolymers can be applied in pure form or else together with conventional excipients to the active ingredient-containing core. Examples of conventional excipients are colored pigments for coloring, white pigments such as titanium dioxide to increase the hiding power, talc and silicon dioxide as non-stick agents, polyethylene glycols, glycerol, propylene glycol, triacetin, triethyl citrate as plasticizer and various surface-active substances such as sodium lauryl sulfate, polysorbate 80, Pluronics and Cremophors, to improve the wetting characteristics. The substances mentioned as examples do not represent a restriction. All additives known to be suitable for gastric fluid-soluble film coatings can be used.

It is also possible to combine the polymers used according to the invention with other film formers or polymers in the ratio from 1:9 to 9:1.

Examples of polymers which can be employed for this purpose are the following:

polyvinylpyrrolidone, polyvinylpyrrolidone copolymers, water-soluble cellulose derivatives such as hydroxypropylcellulose, hydroxypropylmethylcellulose, methylcellulose, hydroxyethylcellulose, acrylate and methacrylate copolymers, polyvinyl alcohols, polyethylene glycols, polyethylene oxide/polypropylene oxide block copolymers.

The coating processes which can be used are the conventional processes such as coating in a fluidized bed or in a horizontal drum coater, the dip-coating process and the pan-coating process. Besides the use for tablets, the polymers according to the invention can also be employed for coating other pharmaceutical preparations such as granules, pellets, crystals or capsules. The novel coating agents are applied in a conventional manner in a thickness of from 5 to 200 $\mu$m, preferably 10 to 100 $\mu$m.

In the use as binder, a distinction is made between wet and dry binders depending on the processing method. The latter are used inter alia for direct tableting and for dry granulation or compaction. In these cases, the binder is mixed with the active ingredient and, where appropriate, other excipients and then directly tableted, or granulated and compacted.

In contrast thereto, in wet granulation the active ingredient/excipient mixture is moistened with a solution of the binder in water or an organic solvent and the moist composition is passed through a sieve and then dried. The moistening and drying may also take place in parallel as, for example, in fluidized bed granulation.

For optimal processing, the binder should have a low viscosity in solution because viscous solutions lead to inhomogeneous granules.

A binder should lead to uniform, hard, non-friable granules or tablets. The hardness is particularly important for tablets because many active ingredients are difficult to compress and thus afford tablets with inadequate mechanical stability.

In addition, the binder should have a negligible adverse effect on the disintegration of the drug forms and the rate of release of the active ingredients.

The most commonly used binders are, for example, polyvinylpyrrolidone, vinyl acetate/vinylpyrrolidone copolymers, gelatin, starch pastes, maltodextrins, hydroxyalkylated or carboxyalkylated cellulose derivatives such as hydroxypropylmethylcellulose, methylcellulose, sodium carboxymethylcellulose, and natural gum types such as, for example, gum arabic, pectin or alginate.

Many of these binders have a high viscosity in solution and are difficult to process. The high viscosity means that the powder particles to be granulated are poorly and non-uniformly wetted, resulting in a granule strength which is too low and a particle size distribution which is unfavorable.

Many binders are, moreover, hygroscopic and swell on absorption of water. This may drastically alter the properties of granules and tablets.

It has now been found, surprisingly, that the polymers according to the invention have excellent effects as binders and, moreover, have a negligible effect on disintegration in concentration ranges from 0.5 to 20% by weight, preferably 1 to 10% by weight, of the total amount of the formulation. Because the graft copolymers have good wetting characteristics, it is moreover possible to improve the release of active ingredients of low solubility.

When the graft copolymers are used as binders, the resulting granules and tablets are exceptionally mechanically stable and also stable on storage for long periods.

The invention also relates to polymers which are obtainable by polymerization of
a) at least one vinyl ester of aliphatic $C_1$–$C_{24}$-carboxylic acids in the presence of
b) polyethers of the general formula I,

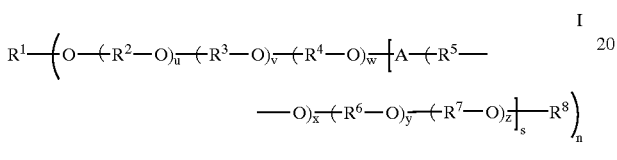

in which the variables have, independently of one another, the following meanings:
$R^1$ hydrogen, $C_1$–$C_{24}$-alkyl, $R^9$—C(=O)—, polyalcohol residue;
$R^8$ hydrogen, $C_1$–$C_{24}$-alkyl, $R^9$—C(=O)—;
$R^2$ to $R^7$
—$(CH_2)_2$—, —$(CH_2)_3$—, —$(CH_2)_4$—, —$CH_2$—CH($CH_3$)—, —$CH_2$—CH($CH_2$—$CH_3$)—, —$CH_2$—CHOR$^{10}$—$CH_2$—;
$R^9$ $C_1$–$C_{24}$-alkyl;
$R^{10}$ hydrogen, $C_1$–$C_{24}$-alkyl, $R^9$—C(=O)—;
A —C(=O)—O—, —C(=O)—B—C(=O)—O—;
B —$(CH_2)_t$—, arylene, optionally substituted;
n 1 to 8;
s 1 to 500;
t 1 to 12;
u 1 to 5000;
v 0 to 5000;
w 0 to 5000;
x 1 to 5000;
y 0 to 5000;
z 0 to 5000.

The invention moreover relates to polymers which are obtainable by polymerization of
a) at least one vinyl ester of aliphatic $C_1$–$C_{24}$-carboxylic acids in the presence of
b) polyethers of the general formula Ia,

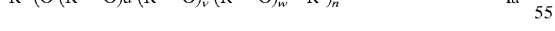

in which the variables have, independently of one another, the following meanings:
$R^1$ hydrogen, $C_1$–$C_{24}$-alkyl, $R^9$—C(=O)—, polyalcohol residue;
$R^8$ hydrogen, $C_1$–$C_{24}$-alkyl, $R^9$—C(=O)—;
$R^2$ to $R^4$
—$(CH_2)_2$—, —$(CH_2)_3$—, —$(CH_2)_4$—, —$CH_2$—CH($CH_3$)—, —$CH_2$—CH($CH_2$—$CH_3$)—;
$R^9$ $C_1$–$C_{24}$-alkyl;
n 1 to 8;
u 1 to 5000;
v 0 to 5000;
w 0 to 5000
together with
c) at least one monomer, selected from the group of
$c_1$) $C_1$–$C_{24}$-alkyl esters of monoethylenically unsaturated $C_3$–$C_8$-carboxylic acids;
$c_2$) $C_1$–$C_{24}$-hydroxyalkyl esters of monoethylenically unsaturated $C_3$–$C_8$-carboxylic acids;
$c_3$) $C_1$–$C_{24}$-alkyl vinyl ethers;
$c_4$) N-vinyllactams;
$c_5$) monoethylenically unsaturated $C_3$–$C_8$-carboxylic acids.

Preferred polymers are obtainable by polymerization of
a) at least one vinyl ester of aliphatic $C_1$–$C_{12}$-carboxylic acids in the presence of
b) polyethers of the general formula Ia, in which the variables have, independently of one another, the following meanings:
$R^1$ hydrogen, $C_1$–$C_{12}$-alkyl, polyalcohol residue;
$R^8$ hydrogen, $C_1$–$C_{12}$-alkyl;
$R^2$ to $R^4$
—$(CH_2)_2$—, —$(CH_2)_3$—, —$(CH_2)_4$—, —$CH_2$—CH($CH_3$)—, —$CH_2$—CH($CH_2$—$CH_3$)—;
n 1 to 5;
u 2 to 2000;
v 0 to 2000;
w 0 to 2000
together with
c) at least one monomer selected from the group of
$c_1$) $C_1$–$C_{12}$-alkyl esters of monoethylenically unsaturated $C_3$–$C_8$-carboxylic acids;
$c_2$) $C_1$–$C_{12}$-hydroxyalkyl esters of monoethylenically unsaturated $C_3$–$C_8$-carboxylic acids;
$c_3$) $C_1$–$C_{12}$-alkyl vinyl ethers;
$c_4$) N-vinyllactams;
$c_5$) monoethylenically unsaturated $C_3$–$C_8$-carboxylic acids.

Very particularly preferred graft copolymers are obtainable by grafting of
a) at least one vinyl ester of aliphatic $C_1$–$C_6$-carboxylic acids in the presence of
b) polyethers of the general formula Ia, in which the variables have, independently of one another, the following meanings:
$R^1$ and $R^8$
hydrogen, $C_1$–$C_6$-alkyl;
$R^2$ to $R^4$
—$(CH_2)_2$—, —$(CH_2)_3$—, —$(CH_2)_4$—, —$CH_2$—CH($CH_3$)—, —$CH_2$—CH($CH_2$—$CH_3$)—;
n 1;
u 2 to 500;
v 0 to 500;
w 0 to 500
together with
c) at least one monomer selected from the group of
$c_1$) $C_1$–$C_6$-alkyl esters of monoethylenically unsaturated $C_3$–$C_6$-carboxylic acids;
$c_4$) N-vinylpyrrolidone, N-vinylimidazole, N-vinylcaprolactam;
$c_5$) (meth)acrylic acid.

The invention likewise relates to polymers which are obtainable by polymerization of
a) at least one vinyl ester of aliphatic $C_1$–$C_{24}$-carboxylic acids in the presence of
b) polyglycerol of the general formula Ib,

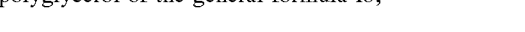

in which the variables have, independently of one another, the following meanings:

R$^1$ hydrogen, C$_1$-C$_{24}$-alkyl, R$^9$—C(=O)—, polyalcohol residue;

R$^8$ and R$^{10}$
   hydrogen, C$_1$-C$_{24}$-alkyl, R$^9$—C(=O)—;

R$^9$ C$_1$-C$_{24}$-alkyl;

n 1 to 8;

u 1 to 2000.

Preferred polymers are obtainable by polymerization of a) at least one vinyl ester of aliphatic C$_1$-C$_{12}$-carboxylic acids in the presence of b) polyglycerol of the general formula Ib, in which the variables have, independently of one another, the following meanings:

R$^1$ hydrogen, C$_1$-C$_{12}$-alkyl, polyalcohol residue;

R$^8$ and R$^{10}$
   hydrogen, C$_1$-C$_{12}$-alkyl;

n 1 to 5;

u 1 to 500.

Particularly preferred polymers are obtainable by polymerization of a) at least one vinyl ester of aliphatic C$_1$-C$_6$-carboxylic acids in the presence of b) polyglycerol of the general formula Ib, in which the variables have, independently of one another, the following meanings:

R$^1$, R$^8$ and R$^{10}$
   hydrogen, C$_1$-C$_6$-alkyl;

n 1;

u 1 to 100.

Besides the linear polyglycerols of the general formula II, it is also possible to use branched and/or cyclic polyglycerols as grafting base.

The graft copolymers based on polyglycerol can be prepared by using for the grafting, in addition to the vinyl esters, at least one other monomer c) selected from the group of c$_1$) C$_1$-C$_{24}$-alkyl esters of monoethylenically unsaturated C$_3$-C$_8$-carboxylic acids;

c$_2$) C$_1$-C$_{24}$-hydroxyalkyl esters of monoethylenically unsaturated C$_3$-C$_8$-carboxylic acids;

c$_3$) C$_1$-C$_{24}$-alkyl vinyl ethers;

c$_4$) N-vinyllactams;

c$_5$) monoethylenically unsaturated C$_3$-C$_8$-carboxylic acids.

Preferred monomers c) are C$_1$-C$_6$-alkyl esters of monoethylenically unsaturated C$_3$-C$_8$-carboxylic acids, N-vinylpyrrolidone, N-vinylimidazole, N-vinylcaprolactam and (meth)acrylic acid.

For a detailed illustration of the graft copolymers based on polyethers of the formula Ia and based on polyglycerol of the formula Ib, including the preferred embodiments, reference may be made to the description given at the outset.

The production and use of the graft copolymers according to the invention are illustrated in detail in the following examples without, however, restricting the invention to the examples.

Preparation of the Graft Copolymers

EXAMPLE 1

72 g of polyethylene glycol (average molecular weight 6000, Pluriol® E 6000) were introduced into a polymerization vessel and heated to 80° C. with stirring under a gentle stream of nitrogen. While stirring and maintaining at 80° C., 410 g of vinyl acetate were added dropwise over the course of 3 h and, at the same time, a solution of 1.4 g of tert-butyl perpivalate in 30 g of methanol was added dropwise, likewise over the course of 3 h. After the addition was complete, the mixture was stirred at 80° C. for 2 h. After cooling, the polymer was dissolved in 450 ml of methanol. For the hydrolysis, 50 ml of a 10% strength methanolic sodium hydroxide solution were added at 30° C. After about 40 min., the reaction was stopped by adding 750 ml of 1% strength acetic acid. The solution was steam distilled to remove the methanol. The clear solution was then freeze dried to result in a white powder. A 20% aqueous solution of the resulting polymer had a viscosity of 124 mPas. The K value was 54, and the ultimate elongation was 74%.

EXAMPLE 2

30 g of polyethylene glycol (average molecular weight 6000, Pluriol® E 6000) were introduced into a polymerization vessel and heated to 80° C. with stirring under a gentle stream of nitrogen. While stirring and maintaining at 80° C., 570 g of vinyl acetate were added dropwise simultaneously with a solution of 2 g of tert-butyl perpivalate in 45 g of methanol over the course of 3 h. After the addition was complete, the mixture was stirred at 80° C. for 2 h. After cooling, the polymer was dissolved in 550 ml of methanol. For the hydrolysis, 65 ml of a 10% by weight methanolic sodium hydroxide solution were added at 30° C. After about 40 min, the reaction was stopped by adding 500 ml of 1% strength acetic acid. The solution was steam distilled to remove the methanol. The clear solution was then freeze dried to result in a white powder. A 20% by weight aqueous solution of the resulting polymer had a viscosity of 46 mPas. The K value was 73, and the ultimate elongation was 171%.

EXAMPLE 3

100 g of polyethylene glycol (average molecular weight 9000) were introduced into a polymerization vessel and heated to 80° C. with stirring under a gentle stream of nitrogen. While stirring and maintaining at 80° C., 300 g of vinyl acetate were added dropwise simultaneously with a solution of 1.5 g of tert-butyl perpivalate in 30 ml of methanol over the course of 3 h. After the addition was complete, polymerization was continued at 80° C. for 2 h. After cooling, the polymer was dissolved in 400 ml of methanol. For the hydrolysis, 40 ml of a 10% by weight methanolic sodium hydroxide solution were added at 30° C. After about 40 min., the reaction was stopped by adding 550 ml of 1% strength acetic acid. The solution was steam distilled to remove the methanol. The clear solution was then freeze dried to result in a white powder. A 20% by weight aqueous solution of the resulting polymer had a viscosity of 199 mPas. The K value was 58, and the ultimate elongation was 225%.

EXAMPLE 4

60 g of polyglycerol (average molecular weight 2200) were introduced into a polymerization vessel and heated to 80° C. with stirring under a gentle stream of nitrogen. While stirring and maintaining at 80° C., 340 g of vinyl acetate were added dropwise simultaneously with a solution of 1.2 g of tert-butyl perpivalate in 30 ml of methanol over the course of 3 h. After the addition was complete, polymerization was continued at 80° C. for 2 h. After cooling, the polymer was dissolved in 400 ml of methanol. For the hydrolysis, 40 ml of a 10% by weight methanolic sodium hydroxide solution were added at 30° C. After about 40 min., the reaction was stopped by adding 640 ml of 1% strength acetic acid. The solution was steam distilled to remove the methanol. The clear solution was then freeze dried to result in a white powder. A 20% by weight aqueous solution of the resulting polymer had a viscosity of 199 mPas. The K value was 66, and the ultimate elongation was 313%.

EXAMPLE 5

60 g of polyethylene glycol/polypropylene glycol block copolymer (average molecular weight about 8000) were introduced into a polymerization vessel and heated to 80° C. with stirring under a gentle stream of nitrogen. While stirring and maintaining at 80° C., 340 g of vinyl acetate were added dropwise simultaneously with a solution of 1.2 g of tert-butyl perpivalate in 30 ml of methanol over the course of 3 h. After the addition was complete, polymerization was continued at 80° C. for 3 h. After cooling, the polymer was dissolved in 400 ml of methanol. For the hydrolysis, 40 ml of a 10% by weight methanolic sodium hydroxide solution were added at 30° C. After about 40 min., the reaction was stopped by adding 650 ml of 1% strength acetic acid. The solution was steam distilled to remove the methanol. The clear solution was then freeze dried to result in a white powder. A 20% by weight aqueous solution of the resulting polymer had a viscosity of 145 mPas. The K value was 45, and the ultimate elongation was 110%.

EXAMPLE 6

60 g of polyethylene glycol (average molecular weight about 6000) were introduced into a polymerization vessel and heated to 80° C. with stirring under a gentle stream of nitrogen. While stirring and maintaining at 80° C., 332 g of vinyl acetate and 8 g of methyl methacrylate were added dropwise over the course of 3 h and, at the same time, a solution of 1.2 g of tert-butyl perpivalate in 30 ml of methanol was added dropwise, likewise over the course of 3 h. After the addition was complete, polymerization was continued at 80° C. for 2 h. After cooling, the polymer was dissolved in 400 ml of methanol. For the hydrolysis, 40 ml of a 10% by weight methanolic sodium hydroxide solution were added at 30° C. After about 40 min., the reaction was stopped by adding 600 ml of 1% strength acetic acid. The solution was steam distilled to remove the methanol. The clear solution was then freeze dried to result in a white powder. A 20% strength aqueous solution of the resulting polymer had a viscosity of 144 mPas. The K value was 56, and the ultimate elongation was 122%.

EXAMPLE 7

Production of propranolol HCl film-coated tablets (coating soluble in gastric fluid)

A film coating of the following composition

| | |
|---|---|
| PEG 6000/VAc graft copolymer from Example 1 | 10.0% by weight |
| Sicovit ® red (from BASF AG) | 1.5% by weight |
| Titanium dioxide BN 56 (from Kronos) | 3.0% by weight |
| Talcum powder (from Riedel de Haen) | 4.5% by weight |
| Water | 81.0% by weight | was sprayed onto 9 mm biconvex tablet cores containing 40 mg of propranolol HCl (from Knoll AG), 195.0 mg of Ludipress® (from BASF AG), 12.50 mg of Kollidon® VA 64 (from BASF AG) and 2.50 mg of magnesium stearate in a horizontal drum coater (Accela-Cota 24", from Manesty).

The spray dispersion was prepared by dissolving the graft copolymer in water, adding Sicovit® red, titanium dioxide and talcum and subsequently homogenizing in a corundum disk mill. 1260 g (including a 10% overage for spray losses) were applied to 5000 g of cores using a spray nozzle with a width of 1.0 mm under a pressure of 2.0 bar and with an inlet air temperature of 60° C. and a spraying rate of 30 g/min. The spraying was followed by drying at 60° C. for 5 min.

The resulting red film-coated tablets were very smooth and glossy and had the following properties:

Appearance: very smooth surface, imprint nicely formed

Disintegration (sim. gastric fluid): 5 min. 26 s.

Difference in disintegration times (film-coated tablet/core): 57 s.

Hardness: 92 N

Difference in hardness (film-coated tablet/core): 23 N

COMPARATIVE EXAMPLE

In analogy to Example 7, Pharmacoat® 606 (hydroxypropylmethylcellulose, from Shin-etsu) was employed in place of the graft copolymer and, as recommended by the manufacturer, 1.0% by weight of polyethylene glycol 6000 (Lutrol® 6000, BASF AG) was added.

Tablets with the following properties were obtained:

Appearance: slightly rough surface, blurred imprint

Disintegration (sim. gastric fluid): 11 min. 12 s.

Difference in disintegration times (film-coated tablet/core): 6 min. 43 s.

Hardness: 87 N

Difference in hardness (film-coated tablet/core): 18 N

EXAMPLE 8

A methyl-PEG 1500/VAc graft copolymer (prepared as in Example 1) was processed as in Example 7. The spray solution used had the following composition:

| | |
|---|---|
| Methyl-PEG 1500/VAc | 20.0% by weight |
| Sicovit ® red (from BASF AG) | 1.5% by weight |
| Titanium dioxide BN 56 (from Kronos) | 3.0% by weight |
| Talcum powder (from Riedel de Haen) | 4.5% by weight |
| Water | 71.0% by weight |

Once again, smooth, slightly glossy, red film-coated tablets were obtained.

Appearance: smooth surface, nicely formed imprint

Disintegration (sim. gastric fluid): 5 min. 35 s.

Difference in disintegration times (film-coated tablet/core): 1 min. 06 s.

Hardness: 94 N

Difference in hardness (film-coated tablet/core): 25 N

COMPARATIVE EXAMPLE

Pharmacoat® 606 was employed in place of methyl-PEG 1500/VAc in analogy to Example 8. It was impossible to spray the solution on because of the extremely high viscosity of Pharmacoat® 606.

EXAMPLE 9
Use as Binder in Glibenclamide Tablets 890 g of calcium hydrogenphosphate (from Rhone Poulenc) and 30 g of glibenclamide (from Arzneimittelwerk Dresden) were passed through a 0.8 mm sieve and mixed in a Turbula mixer (from Bachofen) for 5 min. This powder mixture was moistened slowly with 119 g of a 25% by weight aqueous preparation of a PEG 1500/VAc graft copolymer (prepared as in Example 2) while stirring in a Stephan mixer (from Stephan). To complete the moistening, stirring was continued at 800 rpm for 2 min after addition of the binder preparation. The moist composition was then passed through a 0.8 mm sieve and dried on a tray at 25° C. for 20 h. Addition of 45 g of Kollidon® CL (from BASF) and 5 g of magnesium stearate (from Bärlocher) was followed by final mixing once again in a Turbula mixer for 5 min. This tabletting mixture was then compressed to biplanar, beveled tablets with a diameter of 12 mm and a total weight of 500 mg in a Korsch PH 106 rotary press (from Korsch) under a force of 10 kN and 18 kN.

| Properties: | Force 10 kN | Force 18 kN |
|---|---|---|
| Hardness: | 28 N | 53 N |
| Friability: | 0.7% | 0% |
| Disintegration: | 29 s. | 37 s. |

COMPARATIVE EXAMPLE

Production took place as in Example 9 but with hydroxypropylmethylcellulose (Pharmacoat® 603, from Shin-etsu) as binder, it being necessary for viscosity reasons to reduce the concentration of the binder in the solution to 20% by weight.

| Properties: | Force 10 kN | Force 18 kN |
|---|---|---|
| Hardness: | 16 N | 40 N |
| Friability: | 8.0% | 0.6% |
| Disintegration: | 35 s. | 58 s. |

EXAMPLE 10
Use as Binder in a Hydrochlorothiazide Tablet

A mixture of 8950 g of fine lactose (from Meggle), 350 g of hydrochlorothiazide (from Chemag) and 350 g of Kollidon® CL (from BASF) is sprayed in a WSG 15 fluidized bed granulator (from Glatt) with a binder preparation consisting of 350 g of a polyglycerol 2200/VAc graft copolymer (Example 4) and 3000 g of water, and thus granulated in the fluidized bed.

The settings for the process parameters were as follows:

| | |
|---|---|
| Inlet air temperature: | 90° C. |
| Outlet air temperature | 37° C. |
| Spraying rate | 143 g/min |
| Spraying pressure | 4 bar |

The granulation was followed by drying in the apparatus at 90° C. for 2.5 min. The granules were passed through a 0.8 mm sieve, mixed with 5 g of magnesium stearate (from Bärlocher) and mixed in a Turbula mixer (from Bachofen) for 5 min. Tabletting took place in a Korsch PH 106 (from Korsch) rotary press under a force of 18 kN to give biplanar, beveled tablets with a diameter of 10 mm and a total weight of 300 mg.

Properties of the granules:
Angle of repose: 30°
Appearance: very uniform, negligible fines
Tablet properties:
Hardness: 186 N
Friability: <0.1%
Disintegration: 4 min. 20 s.
Release in sim. gastric fluid (Ph. Eur.) 92% after 15 min.

COMPARATIVE EXAMPLE

Production took place as in Example 10 but with hydroxypropylmethylcellulose (Pharmacoat® 603, from Shin-etsu) as binder.

Properties of the granules:
Angle of repose: 33°
Appearance: somewhat inhomogeneous, some relatively large agglomerates
Tablet properties:
Hardness: 175 N
Friability: 0.2%
Disintegration: 5 min. 10 s.
Release in sim. gastric fluid (Ph. Eur.) 82% after 15 min.

EXAMPLE 11
Use as Ancillary Substance to Produce Ultrasonic Gels 5 g of methyl p-hydroxybenzoate were dissolved in 724 g of demineralized water at 50° C. Then 6 g of polyacrylic acid (Carbopol® 940, from Goodrich) and 15 g of a PEG 9000/VAc graft copolymer (Example 3) were incorporated with stirring. Addition of 200 g of demineralized water and 50 g of 4% strength aqueous sodium hydroxide solution was followed by stirring for 15 min, taking care that no air was incorporated. The resulting gel had a very pleasant skin feel and good contact properties.

EXAMPLE 12
Use as Stabilizer in an Ibuprofen Suspension 250 g of sucrose, 20 g of a Lutrol® F68/VAc graft copolymer (Example 5) and 20 g of sodium citrate were dissolved in demineralized water. Then 80 g of crosslinked polyvinylpyrrolidone (Kollidon® CL-M, BASF AG) and 40 g of ibuprofen 50 (Knoll AG) were stirred in, and the volume was made up to 1000 ml with demineralized water. The resulting low-viscosity, homogeneous white suspension showed sedimentation stability and no aggregation or caking over several weeks.

EXAMPLE 13
Use as Film Former in a Disinfectant Spray 150 g of a PEG 6000/VAc graft copolymer (Example 1) were dissolved in 375 g of demineralized water, and 375 g of ethanol were added. Then 100 g of polyvinylpyrrolidone-iodine (PVP-iodine 30/06, BASF AG) were dissolved with stirring in this polymer solution, and the preparation was used to fill pump spray bottles. The disinfectant spray showed very good film properties on the skin and no loss of iodine after storage under stress conditions (7 days at 52° C.).

We claim:

1. A pharmaceutical presentation comprising the graft polymers obtained by polymerization of
   a) at least one vinyl ester of aliphatic $C_1$–$C_{24}$-carboxylic acids in the presence of b) polyethers of the general formula I,

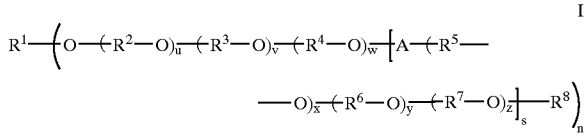

in which the variables have, independently of one another, the following meanings:
R¹ hydrogen, $C_1-C_{24}$-alkyl, $R^9$—C(=O)—, polyalcohol residue;
R⁸ hydrogen, $C_1-C_{24}$-alkyl, $R^9$—C(=O)—;
R² to R⁷ —(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—, —CH$_2$—CHOR$^{10}$—CH$_2$—;
R⁹ $C_1-C_{24}$-alkyl;
R¹⁰ hydrogen, $C_1-C_{24}$-alkyl, $R^9$—C(=O)—;
A —C(=O)—O—, —C(=O)—B—C(=O)—O—, —C(=O)—NH—B—NH—C(=O)—O—;
B —(CH$_2$)$_t$—, arylene, optionally substituted;
n 1 to 8;
s 0 to 500;
u 1 to 5000;
v 0 to 5000;
w 0 to 5000;
x 1 to 5000;
y 0 to 5000;
z 0 to 5000, wherein the molecular weight of the polyethers is in the range from 300 to 100,000,
as coating agent, binder and/or film-forming excipient in pharmaceutical presentations.

2. A pharmaceutical presentation as claimed in claim 1, wherein the graft polymer is obtained by polymerization of
a) at least one vinyl ester of aliphatic $C_1-C_{12}$-carboxylic acids in the presence of
b) polyethers of the general formula I with a number average molecular weight of from 300 to 100,000, in which the variables have, independently of one another, the following meanings:
R¹ hydrogen, $C_1-C_{12}$-alkyl, polyalcohol residue;
R⁸ hydrogen, $C_1-C_{12}$-alkyl;
R² to R⁴ —(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—, —CH$_2$—CHOR$^{10}$—CH$_2$—;
R¹⁰ hydrogen, $C_1-C_{12}$-alkyl;
n 1 to 5;
s 0;
u 2 to 2000;
v 0 to 2000;
w 0 to 2000.

3. A pharmaceutical presentation as claimed in claim 1, wherein the graft polymer is obtained by polymerization of
a) at least one vinyl ester of aliphatic $C_1-C_6$-carboxylic acids in the presence of
b) polyethers of the general formula I with a number average molecular weight of from 500 to 20,000, in which the variables have, independently of one another, the following meanings:
R¹, R⁸ hydrogen, $C_1-C_6$-alkyl;
R² to R⁴ —(CH$_2$)$_2$—, —(CH$_2$)$_3$—, —CH$_2$—CH(CH$_3$)—, —CH$_2$—CHOR$^{10}$—CH$_2$—;
R¹⁰ hydrogen, $C_1-C_6$-alkyl;
n 1;
s 0;
u 5 to 500;
v 0 to 500;
w 0 to 500.

4. A pharmaceutical presentation as claimed in claim 1, wherein, in addition to the vinyl esters a), at least one other monomer c) selected from the group of
c$_1$) $C_1-C_{24}$-alkyl esters of monoethylenically unsaturated $C_3-C_8$-carboxylic acids;
c$_2$) $C_1-C_{24}$-hydroxyalkyl esters of monoethylenically unsaturated $C_3-C_8$-carboxylic acids;
c$_3$) $C_1-C_{24}$-alkyl vinyl ethers;
c$_4$) N-vinyllactams;
c$_5$) monoethylenically unsaturated $C_3-C_8$-carboxylic acids is employed for the polymerization.

5. A pharmaceutical presentation as claimed in claim 1 having a degree of hydrolysis of from 20 to 100% based on the polyvinyl ester groups.

6. A pharmaceutical presentation as claimed in claim 1 having a K value of from 10 to 200.

7. A water-soluble or water-dispersible graft polymer which is obtainable by polymerization of
a) at least one vnyl ester of aliphatic $C_1-C_{24}$-carboxylic acids in the presence of
b) polyethers of the general formula I,

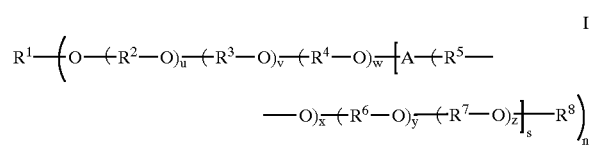

in which the variables have, independently of one another, the following meanings:
R¹ hydrogen, $C_1-C_{24}$-alkyl, $R^9$—C(=O)—, polyalcohol residue;
R⁸ hydrogen, $C_1-C_{24}$-alkyl, $R^9$—C(=O)—;
R² to R⁷
—(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—, —CH$_2$—CHOR$^{10}$—CH$_2$—;
R⁹ $C_1-C_{24}$-alkyl;
R¹⁰ hydrogen, $C_1-C_{24}$-alkyl, $R^9$—C(=O)—;
A —C(=O)—O—, —C(=O)—B—C(=O)—O—;
B —(CH$_2$)$_t$—, arylene, optionally substituted;
n 1 to 8;
s 1 to 500;
t 1 to 12;
u 1 to 5000;
v 0 to 5000;
w 0 to 5000;
x 1 to 5000;
y 0 to 5000;
z 0 to 5000, wherein the molecular weight of the polyethers is in the range from 300 to 100,000.

8. A water-soluble or water-dispersible graft polymer which is obtained by polymerization of
a) at least one vinyl ester of aliphatic $C_1-C_{24}$-carboxylic acids in the presence of
b) polyethers of the general formula Ia,

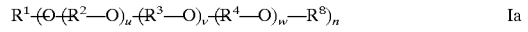

in which the variables have, independently of one another, the following meanings:
R¹ hydrogen, $C_1-C_{24}$-alkyl, $R^9$—C(=O)—, polyalcohol residue;

$R^8$ hydrogen, $C_1$–$C_{24}$-alkyl, $R^9$—C(=O)—;
$R^2$ to $R^4$ —(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—;
$R^9$ $C_1$–$C_{24}$-alkyl;
n 1 to 8;
u 1 to 5000;
v 0 to 5000;
w 0 to 5000, wherein the molecular weight of the polyethers is in the range from 300 to 100,000, together with
c) at least one monomer selected from the group of
  $c_1$) $C_1$–$C_{24}$-alkyl esters of monoethylenically unsaturated $C_3$–$C_8$-carboxylic acids;
  $c_2$) $C_1$–$C_{24}$-hydroxyalkyl esters of monoethylenically unsaturated $C_3$–$C_8$-carboxylic acids;
  $c_3$) $C_1$–$C_{24}$-alkyl vinyl ethers;
  $c_4$) N-vinyllactams;
  $c_5$) monoethylenically unsaturated $C_3$–$C_8$-carboxylic acids.

9. A polymer as claimed in claim 8, which is obtained by polymerization of
a) at least one vinyl ester of aliphatic $C_1$–$C_{12}$-carboxylic acids in the presence of
b) polyethers of the general formula Ia, in which the variables have, independently of one another, the following meanings:
  $R^1$ hydrogen, $C_1$–$C_{12}$-alkyl, polyalcohol residue;
  $R^8$ hydrogen, $C_1$–$C_{12}$-alkyl;
  $R^2$ to $R^4$ —(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—;
  n 1 to 5;
  u 2 to 2000;
  v 0 to 2000;
  w 0 to 2000
  together with
c) at least one monomer selected from the group of
  $c_1$) $C_1$–$C_{12}$-alkyl esters of monoethylenically unsaturated $C_3$–$C_8$-carboxylic acids;
  $c_2$) $C_1$–$C_{12}$-hydroxyalkyl esters of monoethylenically unsaturated $C_3$–$C_8$-carboxylic acids;
  $c_3$) $C_1$–$C_{12}$-alkyl vinyl ethers;
  $c_4$) N-vinyllactams;
  $c_5$) monoethylenically unsaturated $C_3$–$C_8$-carboxylic acids.

10. A polymer as claimed in claim 8, which is obtained by polymerization of
a) at least one vinyl ester of aliphatic $C_1$–$C_6$-carboxylic acids in the presence of
b) polyethers of the general formula Ia, in which the variables have, independently of one another, the following meanings:
  $R^1$ and $R^8$ hydrogen, $C_1$–$C_6$-alkyl;
  $R^2$ to $R^4$ —(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—;
  n 1;
  u 2 to 500;
  v 0 to 500;
  w 0 to 500
  together with
c) at least one monomer selected from the group of
  $c_1$) $C_1$–$C_6$-alkyl esters of monoethylenically unsaturated $C_3$–$C_8$-carboxylic acids;
  $c_4$) N-vinylpyrrolidone, N-vinylimidazole, N-vinylcaprolactam;
  $c_5$) (meth)acrylic acid.

11. A polymer as claimed in claim 7 with a degree of hydrolysis of from 20 to 100% based on the polyvinyl ester groups.

12. A polymer as claimed in claim 7 with a K value of from 10 to 200.

13. A water-soluble or water-dispersible graft polymer which is obtained by polymerization of
a) at least one vinyl ester of aliphatic $C_1$–$C_{24}$-carboxylic acids in the presence of
b) polyglycerol of the general formula Ib, $$R^1\text{—}(O\text{—}(CH_2\text{—}CHOR^{10}\text{—}CH_2\text{—}O)_u\text{—}R^8)_n \qquad \text{Ib}$$

in which the variables have, independently of one another, the following meanings:
  $R^1$ hydrogen, $C_1$–$C_{24}$-alkyl, $R^9$—C(=O)—, polyalcohol residue;
  $R^8$ and $R^{10}$ hydrogen, $C_1$–$C_{24}$-alkyl, $R^9$—C(=O)—;
  $R^9$ $C_1$–$C_{24}$-alkyl;
  n 1 to 8;
  u 1 to 2000, wherein the molecular weight of the polyethers is in the range from 300 to 100,000.

14. A polymer as claimed in claim 13, which is obtained by polymerization of
a) at least one vinyl ester of aliphatic $C_1$–$C_{12}$-carboxylic acids in the presence of
b) polyglycerol of the general formula Ib, in which the variables have, independently of one another, the following meanings:
  $R^1$ hydrogen, $C_1$–$C_{12}$-alkyl, polyalcohol residue;
  $R^8$ and $R^{10}$ hydrogen, $C_1$–$C_{12}$-alkyl;
  n 1 to 5;
  u 1 to 500.

15. A polymer as claimed in claim 13, which is obtained by polymerization of
a) at least one vinyl ester of aliphatic $C_1$–$C_6$-carboxylic acids in the presence of
b) polyglycerol of the general formula Ib, in which the variables have, independently of one another, the following meanings:
  $R^1$, $R^8$ and $R^{10}$ hydrogen, $C_1$–$C_6$-alkyl;
  n 1;
  u 1 to 100.

16. A polymer as claimed in claim 13, wherein, in addition to the vinyl esters, at least one other monomer c) selected from the group of
  $c_1$) $C_1$–$C_{24}$-alkyl esters of monoethylenically unsaturated $C_3$–$C_8$-carboxylic acids;
  $c_2$) $C_1$–$C_{24}$-hydroxyalkyl esters of monoethylenically unsaturated $C_3$–$C_8$-carboxylic acids;
  $c_3$) $C_1$–$C_{24}$-alkyl vinyl ethers;
  $c_4$) N-vinyllactams;
  $c_5$) monoethylenically unsaturated $C_3$–$C_8$-carboxylic acids is used for the polymerization.

17. A polymer as claimed in claim 13, wherein, in addition to the vinyl esters, at least one other monomer c) selected from the group of
  $c_1$) $C_1$–$C_6$-alkyl esters of monoethylenically unsaturated $C_3$–$C_8$-carboxylic acids;
  $c_4$) N-vinylpyrrolidone, N-vinylimidazole, N-vinylcaprolactam;
  $c_5$) (meth)acrylic acid is used for the polymerization.

18. A polymer as claimed in claim 13 with a degree of hydrolysis of from 20 to 100% based on the polyvinyl ester groups.

19. A polymer as claimed in claim 13 with a K value of from 10 to 200.

* * * * *

UNITED STATES PATENT AND TRADEMARK OFFICE
CERTIFICATE OF CORRECTION

PATENT NO. : 6,579,953 B1
DATED : June 17, 2003
INVENTOR(S) : Gotsche et al.

It is certified that error appears in the above-identified patent and that said Letters Patent is hereby corrected as shown below:

<u>Title page,</u>
Item [*] Notice, is incorrect. No terminal disclaimer was filed in the subject patent, and the indication otherwise is incorrect.

<u>Column 22,</u>
Line 62, the formula 1a should be:

-- $R^1\!-\!(\!-\!O\!-\!(\!-\!R^2\!-\!O)_u\!-\!(\!-\!R^3\!-\!O)_v\!-\!(\!-\!R^4\!-\!O)_w\!-\![\!-\!A\!-\!(R^5\!-\!O)_x\!-\!(R^6\!-\!O)_y\!-\!(R^7\!-\!O)_z\!-\!]_s\!R^8)_n$ --.

<u>Column 24,</u>
Line 9, the formula 1b should be:

-- $R^1\!-\!(\!-\!O\!-\!(\!-\!R^2\!-\!O)_u\!-\!(\!-\!R^3\!-\!O)_v\!-\!(\!-\!R^4\!-\!O)_w\!-\![\!-\!A\!-\!(R^5\!-\!O)_x\!-\!(R^6\!-\!O)_y\!-\!(R^7\!-\!O)_z\!-\!]_s\!R^8)_n$ --.

Signed and Sealed this

Twenty-first Day of October, 2003

JAMES E. ROGAN
*Director of the United States Patent and Trademark Office*